US005468244A

United States Patent [19]
Attfield et al.

[11] Patent Number: 5,468,244
[45] Date of Patent: Nov. 21, 1995

[54] SURGICAL APPARATUS FOR USE IN JOINT REPLACEMENT SURGERY

[75] Inventors: Stephen F. Attfield, Long Eaton; Andreas Sambatakakis, Off Osmaston Road, both of United Kingdom

[73] Assignee: Howmedica International, Inc., Ireland

[21] Appl. No.: 201,728

[22] Filed: Feb. 25, 1994

Related U.S. Application Data

[63] Continuation of Ser. No. 971,353, Nov. 4, 1992, abandoned.

[30] Foreign Application Priority Data

Nov. 6, 1991 [GB] United Kingdom .................... 9123555

[51] Int. Cl.⁶ ............................................. A61B 17/56
[52] U.S. Cl. ............................................. 606/90; 606/102
[58] Field of Search .......................... 128/20, 774, 782; 33/512; 606/90, 91, 99, 102, 105

[56] References Cited

U.S. PATENT DOCUMENTS

| | | | |
|---|---|---|---|
| 4,201,226 | 5/1980 | Phillips | 128/774 |
| 4,220,163 | 9/1980 | Malek | 128/782 |
| 4,279,260 | 7/1981 | Stump | 128/774 |
| 4,364,389 | 12/1982 | Keller | 606/88 |
| 4,501,266 | 2/1985 | McDaniel | 128/69 |
| 4,938,230 | 7/1990 | Machek et al. | 128/777 |
| 4,968,316 | 11/1990 | Hergenroeder | 606/90 |
| 4,991,566 | 2/1991 | Shulman et al. | 128/17 |
| 5,002,547 | 3/1991 | Poggie et al. | 606/88 |
| 5,116,338 | 5/1992 | Poggie et al. | 606/90 |
| 5,213,112 | 5/1993 | Niwa et al. | 128/774 |

FOREIGN PATENT DOCUMENTS

86/00767  12/1986  European Pat. Off. .

Primary Examiner—Stephen C. Pellegrino
Assistant Examiner—Guy V. Tucker
Attorney, Agent, or Firm—W. Thad Adams, III

[57] ABSTRACT

A joint replacement surgical apparatus including a main body part, first and second tissue engaging plates mounted on the main body part, the first tissue engaging plate being displaceable towards and away from the second tissue engaging plate. At least one of the first and second tissue engaging plates is adapted to be oriented by the tissue engaged thereby. The first and second tissue engaging plates define respectively first and second substantially planer tissue engaging surfaces, each of the tissue engaging surfaces being arranged such that the surfaces face away from each other.

18 Claims, 2 Drawing Sheets

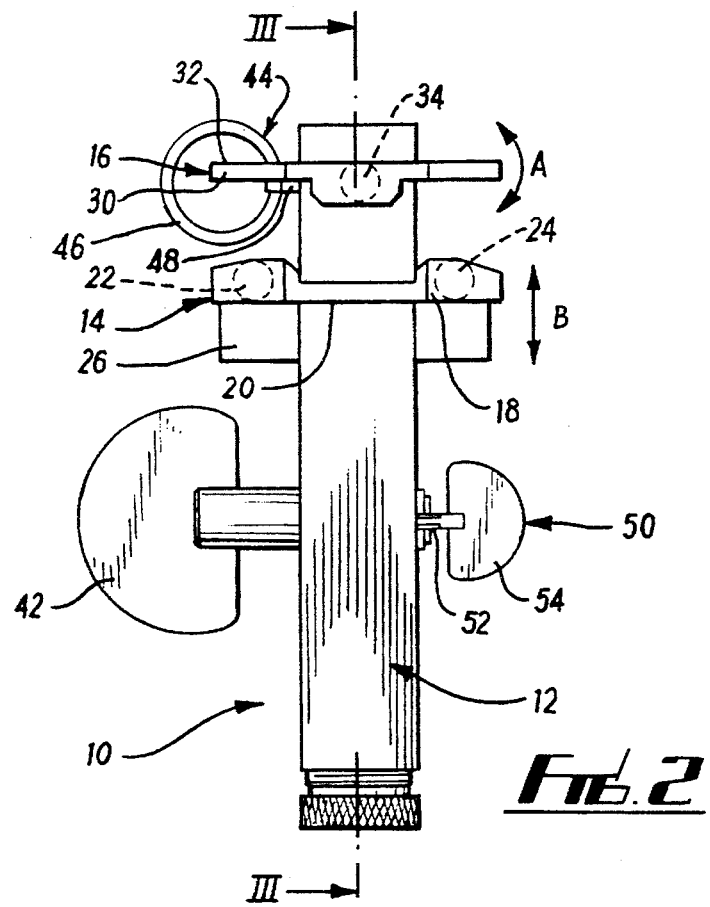
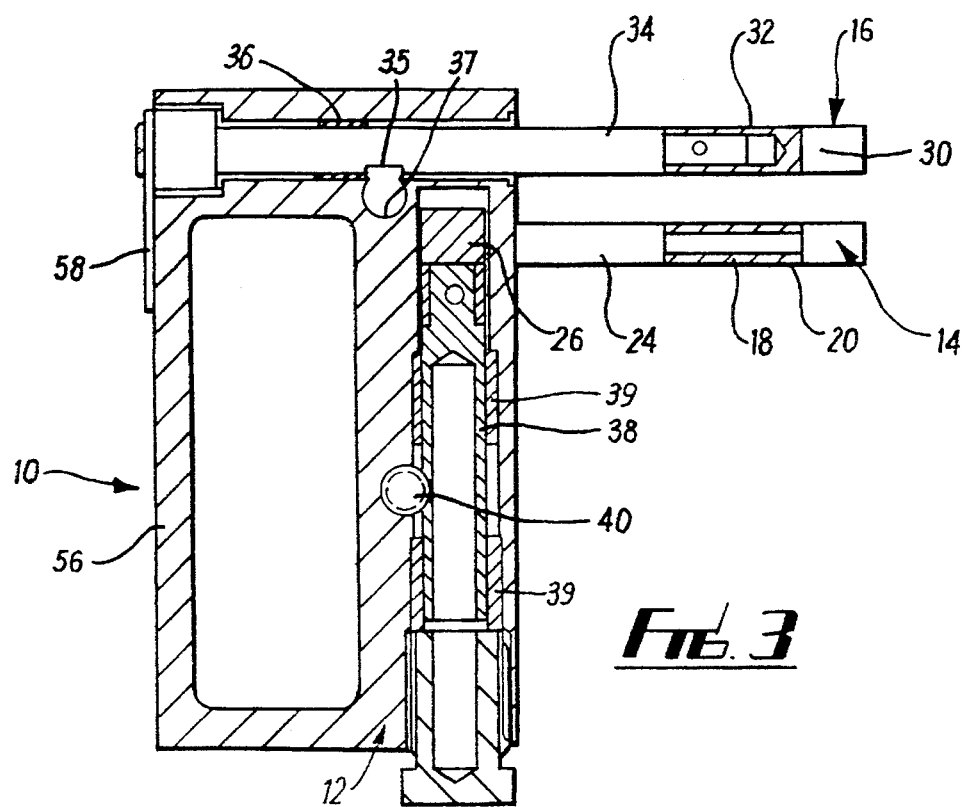

SURGICAL APPARATUS FOR USE IN JOINT REPLACEMENT SURGERY

This application is a continuation of application Ser. No. 07/971,353, filed Nov. 4, 1992, now abandoned.

BACKGROUND OF THE INVENTION

This invention relates to surgical apparatus. Particularly, but not exclusively, this invention relates to surgical apparatus for use in knee surgery and especially total knee arthroplasty.

During total knee arthroplasty, it could be beneficial to eliminate the passive deforming forces around the knee associated with soft tissue imbalance et the time of surgery. Such elimination is achieved by gradual soft tissue releases of the contracted tissues around the knee. In order to carry out this technique successfully, the surgeon has to ensure that the tension of the medial and lateral soft tissue structures of the knee is symmetrically balanced. This is done solely by estimation, which is disadvantageous since if, after surgery, the knee is imbalanced, then failure of prosthesis can result

DESCRIPTION OF RELATED ART

U.S. Pat. No. 4,501,266 discloses a device for use in knee arthroplasty. This device applies measured forces to both the medial and lateral compartments of the knee joint but has the disadvantage that it does not provide any means for determining whether the knee is symmetrically balanced. U.S. Pat. No. 5,116,338 also discloses a device for use in knee surgery. The device enables the surgeon to apply unknown forces to the bones in the knee joint and does not provide any means for determining whether the knee is symmetrically balanced.

SUMMARY OF THE INVENTION

It is an object of this invention to obviate and/or mitigate the disadvantages of these devices.

According to this invention there is provided surgical apparatus comprising first and second tissue engaging means, the first tissue engaging means being displaceable towards and away from the second tissue engaging means, wherein at least one of said first and second tissue engaging means is adapted to be oriented by the tissue engaged thereby.

The surgical apparatus is particularly suitable for use in joint replacement surgery, and in such cases the tissue engaged by the first and second tissue engaging means is bone tissue, for example bone tissue of the tibia and femur in a knee joint.

Preferably, the first and second tissue engaging means define respectively first and second tissue engaging surfaces, which may be substantially planar, and each of said tissue engaging means being desirably arranged such that said surfaces face away from each other.

In a preferred embodiment, only said second tissue engaging means is adapted to be oriented by the tissue engaged thereby. Preferably, said second tissue engaging means is adapted to be rotatably oriented by said tissue engaged thereby.

Measuring means may be provided to measure the degree of deflection of said second tissue engaging surface away from a position of parallelism with the first tissue engaging surface when said first and second tissue engaging means engage the tissue.

Locking means may be provided to lock the second tissue engaging means such that the first tissue engaging surface is parallel with the second tissue engaging surface. The locking means may comprises a pin adapted to engage said second tissue engaging means.

Preferably, the apparatus comprises displacement means to displace the first tissue engaging means towards or away from the second tissue engaging means the displacement means may comprise a gearing arrangement. Preferably, the gearing arrangement comprises a rack and pinion assembly. Securing means may be provided to secure the first tissue engaging means at any desired separation from the second tissue engaging means. Preferably, the securing means comprises a threaded member adapted to engage the displacement means.

The apparatus may comprise a main body part and each of the first and second tissue engaging means may comprises a shaft mounted on the main body part and a plate defining said tissue engaging surface. Preferably, the first tissue engaging means comprises two of said shafts mounted respectively on either side of the main body part and connected to each other by a connecting member. The connecting member is preferably mounted on the displacement means. Preferably the second tissue engaging means comprises only one of said shafts rotatably mounted in the main body part.

Preferably, the measuring means is connected to the shaft of the first tissue engaging means and may comprise a vernier scale. Alternatively, the measuring means may be electronic and may comprise a suitable transducer.

The main body part may include a handle to enable the apparatus to be manipulated manually.

An embodiment of the invention will now be described by way of example only with reference to the accompanying drawings in which:

BRIEF DESCRIPTION OF THE DRAWINGS

FIG. 2 is a front view of the apparatus shown in FIG. 1; and

FIG. 3 is a sectional view along the lines III—III in FIG. 2.

DESCRIPTION OF THE PREFERRED EMBODIMENT

Figure 1:
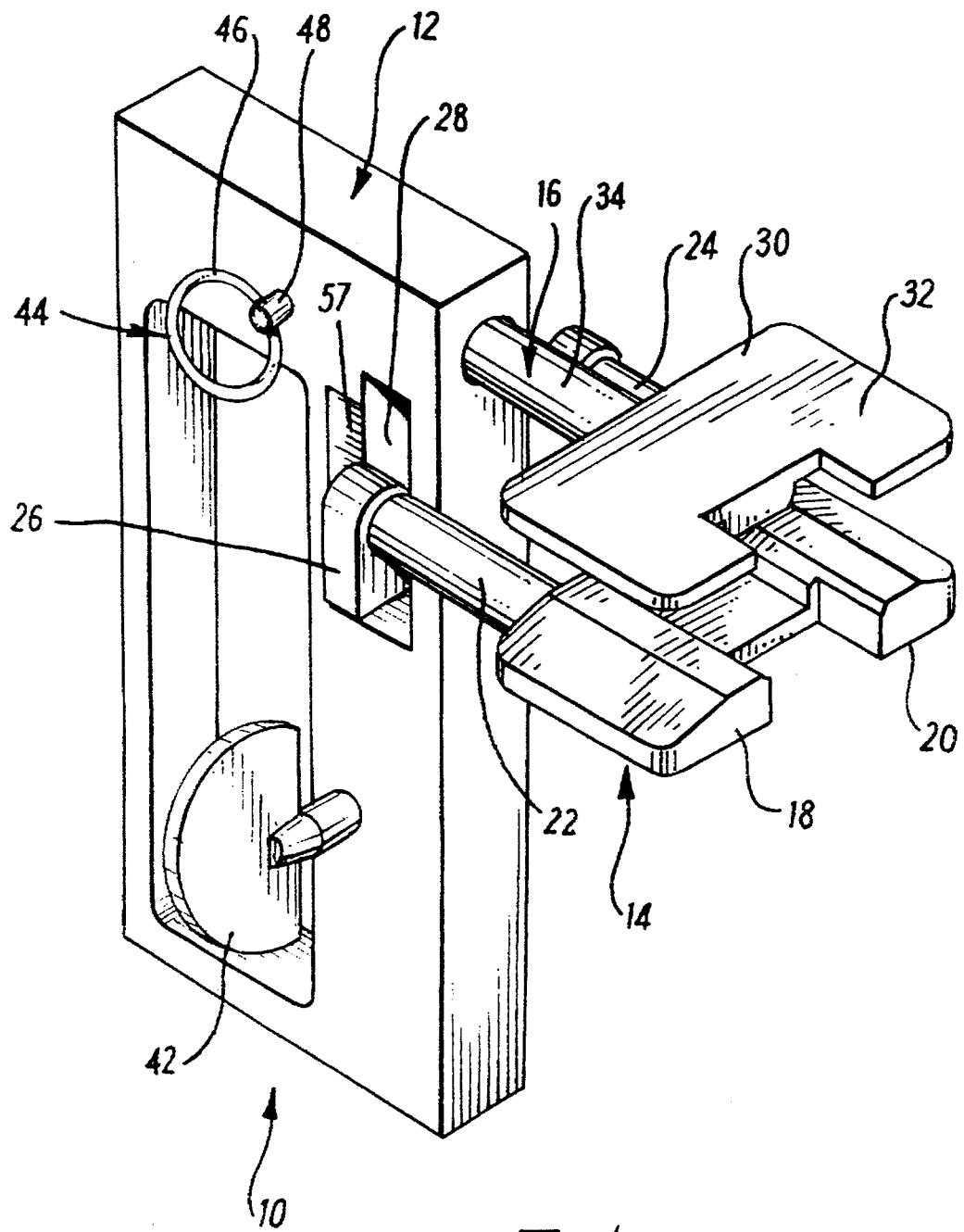
FIG. 1 is a perspective view of a surgical apparatus.

Referring to the drawings, there is shown surgical apparatus 10 for use in knee surgery. The apparatus 10 comprises a main body 12, and first and second tissue engaging means 14,16. The first tissue engaging means 14 comprises a first plate 18 defining a first tissue engaging surface 20 which faces downwardly in the example shown in FIG. 1. The first tissue engaging means 14 also includes two shafts 22,24 which connect the first plate 18 to the main body 12 and extend on either side of the main body 12. A connecting means 26 extends through an aperture 28 in the main body 12 to connect the shafts 22,24 together.

The second tissue engaging means 16 comprises a second plate 30 defining a second tissue engaging surface 32. The second tissue engaging surface 32 faces in the opposite direction to the first tissue engaging surface 20, as shown in the drawings. The second tissue engaging means 16 includes a shaft 34 extending from the plate 30 into the main body part 12 in which it is rotatably mounted in low friction bushes 36 such that it can rotate in the directions shown by the double headed arrow A (see FIG. 2).

The first tissue engaging means 14 is displaceable towards and away from the second tissue engaging means 16 in the directions shown by the double headed arrow B in FIG. 2. Displacement means in the form of a rack 38 and a pinion 40 are provided to displace the first tissue engaging means 14 in the directions shown by the arrow B. A key 42 is used to turn the pinion 40 to displace the first tissue engaging means 14. The rack 38 is mounted in low friction bushes 39.

Securing means 50 is provided to secure the first tissue engaging means 14, at any desired separation from the second tissue engaging means 16. Locking means 44 is provided to lock the second tissue engaging means 16 such that the second tissue engaging surface 32 is parallel to the first tissue engaging surface 20.

The locking means 44 comprises a pin 48 having a looped head 46 and can be received in the main body 12 through a bore 37. The pin 48 is substantially cylindrical in configuration and is provided with a planar portion adapted to engage a correspondingly planar portion 35 on the shaft 34. When the pin 48 is inserted into the main body 12, the planar portion on the pin 48 and the planar portion on the shaft 34, engage each other to lock the second tissue engaging means 16 such that the second tissue engaging surface 32 is parallel to the first tissue engaging surface 20.

The securing means 50 comprises a threaded member 52 having a handle 54. The threaded member 52 is threadably received in the main body 12 and by screwing the threaded member 52 into the main body 12 by means of the key 54, the threaded member 52 can engage the rack and pinion 38,40 to secure the first tissue engaging means at any desired separation from the second tissue engaging means thereby preventing the first and second tissue engaging means 14,16 from being closed under the tension of the soft tissue surrounding the knee.

The main body 12 is provided with a handle 56 to enable the apparatus to be held by a surgeon for appropriate manipulation.

Measuring means in the form of a first vernier scale 57 is provided on the main body 12 (see FIG. 1) to measure the amount of displacement of the first tissue engaging means, and thereby measure the mean distance between the first arid second tissue engaging surfaces 18,32.

A second vernier scale 58 is provided at the rear of the main body 12 connected to the second shaft 34. The vernier scale 58 measures the angle of rotation of the second tissue engaging means 16.

Alternatively, the second shaft 34 and the rack 38 can be connected to suitable electronic measuring means, for example a transducer, to measure the angle of deflection and the mean separation distance.

In knee replacement surgery, the end portions of the femur and tibia are removed, before the prosthesis knee joint is fitted. In order to fit the prosthesis correctly, it is necessary to ensure by surgery that there is no imbalance in the soft tissue around the joint.

In knee surgery, the end portions of the femur and tibia are removed to leave a planar end surface on the end of each of the bones. In order to determine whether there is any imbalance in the soft tissue, and if so, how much, the surgical apparatus 10 is used. The first and second plates 18,30 are inserted between the planar ends of the femur and tibia, and the first plate 18 is then adjusted towards the end of the tibia by turning the key 42. The key 42 is continued to be turned until both plates 18,30 engage respectively the tibia and the femur, and further continued rotation of the key 42 will cause the femur and tibia to be moved apart to tension the soft tissue surrounding the knee joint. Any imbalance in the soft tissue will mean that the planar ends of the femur and tibia will not be parallel thus causing the second plate 30 to be rotated relative to the first plate 18. The amount of imbalance in the soft tissue can then be determined from the angle of deflection of the second plate 30. The device 10 is removed and the surgeon can then surgically release the tensions in the soft tissue thereby remove any imbalance. The device 10 is then inserted in the joint to measure the amount of imbalance and the process can be repeated until the imbalance has been completely removed.

The apparatus 10 has an alternative use in which the second tissue engaging means 16 is locked such that the first tissue engaging service 20 remains parallel with the second tissue engaging surface 32 on the second plate 26. With the second tissue engaging means 16 so locked, the apparatus 10 can be used as an adjustable spacer to assess joint stability. In order to do this, the first and second plates 18,26 are inserted into the place where the surgery is to be performed and by appropriate turning of the key 42 the soft tissue can be moved apart by the first and second plates 18,30.

Various modifications can be made to the apparatus without departing from the scope of the invention. For example, the second plate 30 could be fixed in position and the first plate 18, could be movable linearly as described above and also angularly to measure the amount of imbalance. Also a tension spring could be provided on the second tissue engaging means 16 to bias the second plate 30 to a position whereby the first and second tissue engaging surfaces are parallel.

A further modification of the invention is in the use of the apparatus 10 as a means for measuring the tension in the soft tissue around the joint in which it is used. In this modification, a suitable measuring device, such as a strain gauge could be fitted to the first measuring means 14 to determine the forces on the soft tissue around the joint. Also a suitable torque measuring device could be fitted to the second tissue engaging means to measure the torque stability of the knee. Also the second plate 30 could be adapted to rotate relative to the shaft 34, and measurements could be taken with a standard angular measuring means.

It will be appreciated that the use of the device 10 is not restricted to knee surgery but it can be used in surgery of other joints, for example, the hip and elbow.

We claim:

1. Surgical apparatus for use in the surgical replacement of joints between bones, said apparatus comprising:

(a) first planar bone engaging means mounted on a main body part and including a first bone engaging surface adapted to engage one of the bones at said joint;

(b) second planar bone engaging means mounted on the main body part and including a second bone engaging surface facing away from the first bone engaging surface and adapted to engage the other of the bones at said joint;

(c) displacement means for displacing the first bone engaging means away from the second bone engaging means thereby to tension soft tissue between said bones;

(d) wherein at least one of the first and second bone engaging means is adapted to be oriented by the bone engaged thereby upon tensioning of said soft tissue between the bones; and (e) locking means to lock the second bone engaging means such that the second bone engaging surface is parallel to the first bone engaging surface.

2. Surgical apparatus according to claim 1, wherein the locking means comprises a pin adapted to engage said second bone engaging means.

3. Surgical apparatus for use in the surgical replacement of joints between bones, said apparatus comprising:

(a) first bone engaging means mounted on a main body part and including a first planar bone engaging surface adapted to engage one of the bones at said joint;

(b) second bone engaging means mounted on the main body part and including a second planar bone engaging surface facing away from the first bone engaging surface and adapted to engage the other of the bones at said joint;

(c) displacement means for displacing the first bone engaging means away from the second bone engaging means thereby to tension soft tissue between said bones;

(d) wherein only the second bone engaging means is adapted to be oriented by the bone engaged thereby upon tensioning of said soft tissue between the bones and said second bone engaging means is adapted to be rotatably oriented by said bone engaged thereby; and (e) measuring means to measure the degree of deflection of said second bone engaging surface from of the first bone engaging surface when said soft tissue is tensioned.

4. Surgical apparatus according to claim 1 or 3, wherein only said second bone engaging means is adapted to be oriented by the bone engaged thereby.

5. Surgical apparatus according to claim 4, comprising measuring means to measure the degree of deflection of said second bone engaging surface away from a position of parallelism with the first bone engaging surface when said soft tissue is tensioned.

6. Surgical apparatus according to claim 1 or 3, wherein said second bone engaging means is adapted to be rotatably oriented by said bone engaged thereby.

7. Surgical apparatus according to claim 1 or 3, wherein said displacement means comprises a gearing arrangement.

8. Surgical apparatus according to claim 7, wherein the gearing arrangement comprises a rack and pinion assembly.

9. Surgical apparatus according to claim 1 or 3, comprising securing means to secure the first bone engaging means at any desired separation from the second bone engaging means.

10. Surgical apparatus according to claim 9, wherein the securing means comprises a threaded member adapted to engage the displacement means.

11. Surgical apparatus according to claim 1 or 3, wherein each of the first and second bone engaging means comprises at least one shaft mounted on the main body part and a plate defining said bone engaging surface.

12. Surgical apparatus according to claim 11, wherein the first bone engaging means comprises two of said shafts mounted respectively on either side of the main body part and connected to each other by a connecting member, the connecting member being mounted on the displacement means.

13. Surgical apparatus according to claim 12, wherein the main body part includes a handle to enable the apparatus to be manipulated manually.

14. Surgical apparatus according to claim 11, wherein the second bone engaging means comprises only one of said shafts rotatably mounted in the main body part.

15. Surgical apparatus according to claim 11, wherein measuring means is connected to the shaft of the first bone engaging means.

16. Surgical apparatus according to claim 15, wherein the measuring means comprise a vernier scale.

17. Surgical apparatus according to claim 11, comprising further measuring means to measure a angle of rotation of the second bone engaging means.

18. Surgical apparatus according to claim 17, wherein the further measuring means comprises a vernier scale.

* * * * *